United States Patent [19]
Scinto et al.

[11] Patent Number: 5,617,872
[45] Date of Patent: Apr. 8, 1997

[54] HYPERSENSITIVE CONSTRICTION VELOCITY METHOD FOR DIAGNOSING ALZHEIMER'S DISEASE IN A LIVING HUMAN

[75] Inventors: Leonard F. M. Scinto, Cambridge; Kirk R. Daffner, Newton, both of Mass.

[73] Assignee: Beth Israel Hospitcal Assoc. Inc., Boston, Mass.

[21] Appl. No.: 447,630

[22] Filed: May 23, 1995

Related U.S. Application Data

[63] Continuation-in-part of Ser. No. 279,795, Jul. 25, 1994, abandoned.

[51] Int. Cl.$^6$ .................................................. A61B 13/00
[52] U.S. Cl. ............................................................ 128/745
[58] Field of Search ..................................... 128/731, 745, 128/897, 898; 351/205, 221

[56] References Cited

U.S. PATENT DOCUMENTS

| | | | |
|---|---|---|---|
| 4,755,043 | 7/1988 | Carter | 351/205 |
| 4,850,691 | 7/1989 | Gardner et al. | 351/221 |
| 5,187,506 | 2/1993 | Carter | 351/221 |
| 5,297,562 | 3/1994 | Potter | 128/898 |
| 5,305,764 | 4/1994 | Yamada et al. | 128/745 |

OTHER PUBLICATIONS

Paykel et al., *Arch Gen Psych* 51:325–332 (Apr. 1994).
*Clinical Neurology of Aging*, Chap. 2, 1984, pp. 9–52; Albert.
*Dementia*. Chaps. 3 & 6, 1987, pp. 55–67 & 167–176; Whitehouse.
Francis et al., *N Engl J Med* 313:7–11 (1985).
Brion et al., in *Senile Dementia of the Alzheimer's Type*, 1984, pp. 164–174.
Whitehouse et al., *Science* 215: 1237–1239 (1982).
Rozher et al., *J. Cell Biol* 107:2703–2716 (1988).
Rafalowska et al., *Acta Neuropathol* 77:21–25 (1988).
Wisniewski et al., *Acta Neuropathol* 78:22–27 (1989).
Kidd, M., *Brain* 897:307–320 (1964).
Gonatas et al., *J. Neuropath Exp Neurol* 26:25–39 (1967).
Wisniewski et al., *J Neurol Sci* 27:173–181 (1976).
DeSousa et al., *Nature* 319: 593–595 (1986).
Whitehoue et al., *Neuobiology* 37:905–909 (1987).
Cork et al., *J Neuropathol Exp Neurol* 45:56–64 (1986).
Nieto et al., *Acta Neuropathol* 78:47–51 (1989).
Weidmann et al., *Cell* 57:115–126 (1989).
Dyrks et al., *Embo J* 7:949–957 (1988).
Masters et al., *Embo J* 4:2757–2763 (1985).
Ponte et al., *Nature* 331:525–527 (1988).
Kitaguchi et al., *Nature* 331:530–532 (1988).
Tanzi et al., *Nature* 331:528–530 (1988).
Sauvage & Octave, *Science* 245:651–653 (1989).
Tanzi et al., *Science* 235:880–884 (1987).
St–George–Hyslop et al., *Science* 235:885–890 (1987).
Amaducci et al., *Neurobiology* 36:922–931 (1986).
Sacks & Smith, *J. Neurol Neurosurg Psych* 52:1294–1295 (1989).
Goldgaber et al., *Science* 235:877–880 (1987).
Applied Sciences Laboratory January 1992 publication.
Applied Sciences Laboratories January 1993 Addendum & February 1992 Guide To Operation manual.

*Primary Examiner*—Max Hindenburg
*Attorney, Agent, or Firm*—David Prashker

[57] ABSTRACT

The present invention provides a non-invasive method for diagnosing Alzheimer's disease in a living human subject. The diagnostic method employs a non-invasive automated apparatus which can repetitively measure pupil constriction velocity for a pre-chosen duration both before and after stimulation by visible light; and cumulatively record such measured pupil constriction velocity data as is obtained over time. The method also administers at least one neural transmitter mediator to a targeted eye of the living subject in an amount insufficient to cause marked changes in pupillary dynamic response in a person who is not afflicted with Alzheimer's disease. The marked hypersensitivity of an Alzheimer's dementia patient to the administered neural transmitter mediator causes a marked change in pupil constriction velocity and thus serves as the means diagnostically to determine and identify an individual living human subject as being afflicted with Alzheimer's disease.

2 Claims, 5 Drawing Sheets

*CV = CONSTRICTION VELOCITY

HYPERSENSITIVE CONSTRICTION VELOCITY METHOD FOR DIAGNOSING ALZHEIMER'S DISEASE IN A LIVING HUMAN

CROSS-REFERENCE

This application is a Continuing-In-Part of U.S. application Ser. No. 8/279,795 filed Jul. 25, 1994, now abandoned.

FIELD OF THE INVENTION

The present invention is concerned with non-invasive methods for the diagnosis of Alzheimer's Disease in a living human patient; and is particularly directed to observing measuring changes in pupillary dynamics caused by the application of neural transmitter agonists or antagonists to Alzheimer's Disease patients in comparison to cognitively intact, non-Alzheimer's individuals.

BACKGROUND OF THE INVENTION

Alzheimer's Disease ("AD") is a dementing disorder characterized by progressive impairments in memory and cognition typically occurring in later life; and is associated with a multiplicity of structural, chemical and functional abnormalities involving regions of the brain concerned with cognition and memory and particular populations of nerve cells. This form of dementia was first reported by Alois Alzheimer in 1907 when he described a particular disease of the cerebral cortex in a 51-year-old woman suffering from an inexorably progressive dementing disorder. Although other forms of dementia were known and well characterized at the time of Alzheimer's clinical report, his patient was found to be clinically and pathologically unusual, based on the relatively young age of the patient and the presence of the then newly described intra-cellular inclusions which have come to be known as neurofibrillary tangles ("NFTs"). In recognition of this unique combination of clinical and pathological features, the term "Alzheimer's Disease" subsequently came into common usage.

Today, Alzheimer's Disease is considered to be one of the forthcoming scourges of the 21st century. This is due in major part to the aging population in concert with data indicating a marked increase in the incidence of dementia with advancing age; and in part to epidemiologic studies measuring the current prevalence of such disorders which suggest that the dementia occurs in up to 10% of individuals over the age of 65. It is estimated that in the United States alone, as many as 4 million individuals may be affected with Alzheimer's Disease; and the cost of caring for such individuals is well over 80 billion dollars annually and increasing rapidly.

Since the recognition of this form of dementia as a specific disorder, many different neurobiologic approaches have been undertaken to studying and understanding the nature and the mechanism of action for Alzheimer's Disease, with a view to possible future therapeutic treatments and/or prevention. Representative of the range and diversity of these many neurobiologic approaches are those listed within Table A below.

TABLE A

Neurobiologic Approaches to the Study of Alzheimer's Disease*

| Biologic Measures | Methods | Examples |
| --- | --- | --- |
| Brain metabolism | In vivo imaging studies | Reduced glucose utilization in neocortex, esp. parietal and temporal areas |
| Histology of brain | Histochemistry, immunocytochemistry | /A4 immunoreactive plaques in neocortex and hippocampus |
| Quantitation of pathology | Morphometric methods | Reduced number of neurons in basal forebrain cholinergic system |
| Neuron size and Shape | Golgi Stains | Abnormal dendritic arborizations |
| Ultrastructure | Electron microscopy, immunocytochemistry | PHF in NFT and /A4 fibrils in plaques |
| Transmitters and enzymes | Assays of markers | Reduced levels of ChAT, somatostatin, and CRF in cortex |
| Receptors | Binding Assays in vitro autoradiography | Reduced cortical somatostatin receptors and increased cortical CRF receptors |
| Proteins in abnormal organelles | Purification of constituents, analyses of proteins and other components, immunocytochemistry freeze-fracture/deep-etch | Decoration of PHF with antineurofilament and antiau antibodies; tubulinlike immunoreactivity in GVD; actin in Hirano bodies; /A4 in plaque cores and congo philic angiopathy |
| Proteins and their modifications | Immunoblots, immunocytochemistry, in vitro incorporation of amino acids | Phosphorylated 200-kD neurofilament A68 and tau associated with NFT; aberrant processing of APP and PrP amyloid |
| RNAs | Hybridization on gels and in situ; measurements of mRNAs and enzymes acting on RNAs | Reduced mRNA in some cells; PrP and APP mRNA present in neurons |

TABLE A-continued

Neurobiologic Approaches to the
Study of Alzheimer's Disease*

| Biologic Measures | Methods | Examples |
| --- | --- | --- |
| Genes | Recombinant DNA technology | Anonymous marker on chromosome 21 linked to familial AD; APP gene localized to chromosome 21 |

ABBREVIATIONS

| | |
| --- | --- |
| AD | Alzheimer's disease |
| /A4 | -amyloid protein |
| ChAT | choline acetyltransferase |
| CRF | corticotropin-releasing factor |
| GVD | granulovacuolar degeneration |
| kD | kilodalton(s) |
| mRNA | messenger ribonucleic acid(s) |
| NFT | neurofibrillary tangle(s) |
| PHF | paired helical filament(s) |
| PrP | prion protein |

*Source: DEMENTIA (Peter J. Whitehouse, Ed.), F.A. Davis Co., Philadelphia, 1993, Chapter 3, pp. 56–57.

In addition, a great many research studies and clinical investigations have been undertaken to study the structural deficiencies, chemical changes, and functional abnormalities both within the brain and within different populations of nerve cells. The depth of such investigations and studies are represented by the following publications: *DEMENTIA* (Peter J. Whitehouse, Ed.), F. A. Davis Company, Philadelphia. 1993; Paykel, et al., *Arch. Gen. Psychiat.* 51: 325–332 (1994); Amaducci, et al., *Neurology,* 36: 922–931 (1986); McKhann, et al., *Neurology* 34: 939–944 (1984); Heston et al., *Arch. Gen. Psychiatry* 38: 1085–1090 (1981); *Aging of the Brain* (Gispen and Traber, editors), Elsevier Science Publishers, Amsterdam, 1983, pages 275–282: Heyman et al., *Ann. Neurol.* 15: 335–341 (1984); Brayne C. and P. Calloway, *Lancet* 1: 1265–1267 (1988); Roth et al., *Br. J. Psychiatry* 149: 698–709 (1986); Medical Research Council, *Report from the NRC Alzheimer's Disease Workshop*, London, England, 1987; Morris et al., *Neurology* 41: 469–478 (1991); *Aizheimer's Disease: Senile Dimentia and Related Disorders* (Katzman, T. D. and R. L. Bick, editors), Raven Press, New York, 1994, pages 47–51; and the references cited within each of these publications.

In spite of the many research investigations and diverse studies undertaken to date, present clinical evaluations still cannot establish an unequivocal diagnosis of Alzheimer's Disease. To the contrary, the only presently known means for positively proving and demonstrating Alzheimer's Disease in a patient can only be achieved by a brain biopsy or a post-mortem examination to assess and determine the presence of neurofibrillary tangles (NFT) and senile (amyloid) plaques in brain tissue. These criteria for the definite diagnosis of Alzheimer's Disease are met only by histologic evidence.

Instead, a set of criteria for the diagnosis of probable Alzheimer's Disease have been described and include: (1) the presence of a dementia syndrome with defects in two or more areas of cognition; (2) progressive worsening of memory and other cognitive function over time; (3) a relatively intact level of consciousness; (4) age at disease onset at a time between 40 and 90 years of age; and (5) the specific absence of any other systemic or central nervous system process that could account for the progressive cognitive deterioration in the individual.

In addition, the probability of an accurate diagnosis in the living patient is augmented by laboratory examinations (such as VDRL and TFT) and by imaging studies (such as computed tomography and magnetic resonance imaging). Such laboratory examinations and/or imaging studies demonstrate the existence and effects of other causes of dementia (such as subdural hematoma, intracranial tumors, infection and brain infarction) and disclose results which are consistent with but are not themselves diagnostic of Alzheimer's Disease. Nevertheless, present clinical diagnoses are wrong in as many as 45% of cases. Thus, there is no sound basis or reliable test methodology at all today for the diagnosis of definite Aizheimer's Disease other than the microscopic examination of histologic material from brain biopsy or autopsy material. Instead, the best clinical diagnosis available to date is only a presumptive determination based on criteria which are evaluations of cognitive and neurological functions for that patient.

It is therefore overwhelmingly clear that there has been and remains today a long standing need for an accurate method to diagnose Alzheimer's Disease clinically in a living human subject with substantial certainty and reliability. In addition, were such a diagnostic methodology also able to be non-invasive, rapid in time required for performance, and precise via the accumulation of large quantities of empirical data, such a diagnostic methodology would be recognized by physicians and laymen alike as being a major advance and substantial improvement in this field.

SUMMARY OF THE INVENTION

The present invention is a non-invasive method for diagnosing Alzheimer's disease in a living human subject. This diagnostic method comprises the steps of:

providing non-invasive apparatus means for
(a) introducing photostimulating visible light of predetermined wavelength, duration and intensity to the eye on-demand sufficient to cause a constriction of the pupil, and
(b) determining the velocity of pupil constriction caused by said introduced photostimulating visible light;

identifying one eye in the living human subject as a targeted eye;

administering at least one neural transmitter mediator to said targeted eye of the living human subject in an amount insufficient to cause a marked change in pupillary dynamic response in a person not afflicted with Alzheimer's disease, said neural transmitter mediator being selected from the group consisting of cholinergic antagonists and agonists;

waiting a predetermined interval of time for said administered neural transmitter mediator to act upon said targeted eye; then introducing photostimulating visible light of predetermined wavelength, duration and intensity to the targeted eye sufficient to cause a constriction of the pupil using said non-invasive apparatus means; and determining pupil constriction velocity for said photostimulated targeted eye using said non-invasive apparatus means, a marked decrease in pupil constriction velocity for said targeted eye with respect to a preestablished normative standard diagnostically establishing that living human subject as being afflicted with Alzheimer's disease.

BRIEF DESCRIPTION OF THE DRAWING

The present invention may be more easily and completely understood when taken in conjunction with the accompanying drawing, in which.

DETAILED DESCRIPTION OF THE INVENTION

Figure 1:
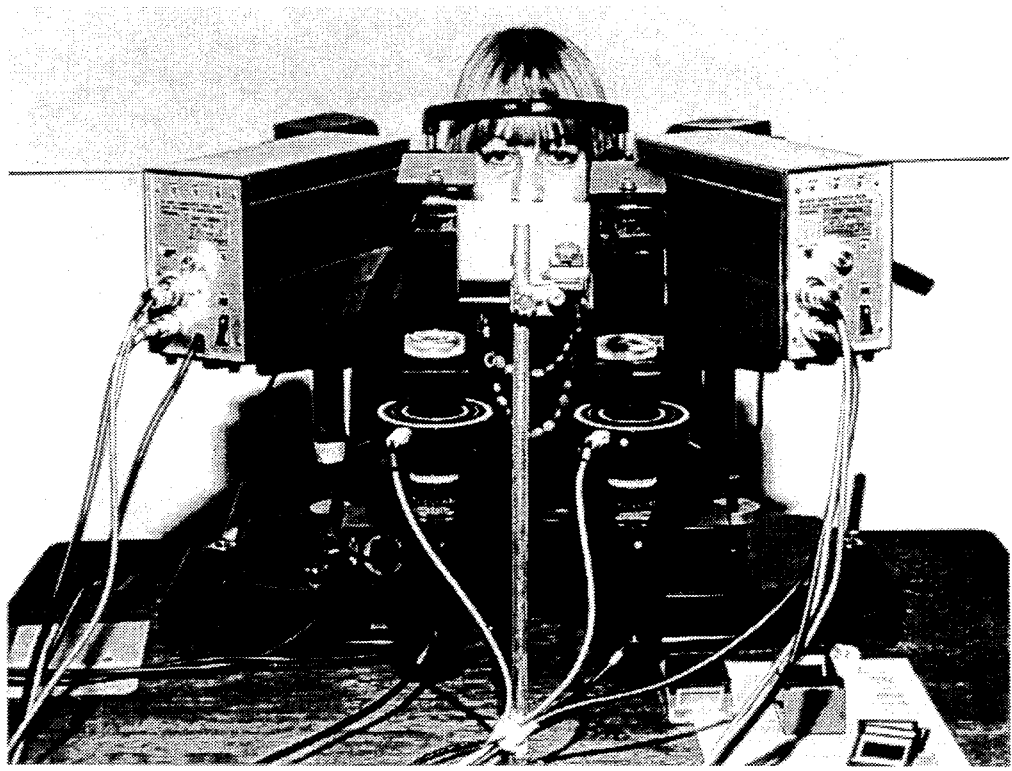
FIG. 1 is a photograph showing the Series 1000 Photostimulator/Controller and Series 1050 TV Pupillometer in combination.

The present invention is a non-invasive method for diagnosing Alzheimer's disease in a living human subject performed via a precise measurement of pupil constriction velocity in response to stimulation by a predetermined intensity and duration of visible light energy. As will be described in detail hereinafter, this diagnostic method relies upon and takes advantage of a newly appreciated recognition that some aspects of the typical Alzheimer Disease patient's autonomic nervous system are hypersensitive to neural transmitter mediators administered specifically to the eye; and utilizes the differences in pupillary dynamic response to stimulation by a known quantity and duration of light between Alzheimer's patients and cognitively intact persons to such pharmacologically active agents as an empirical basis and standard for accurately, positively and definitely diagnosing Alzheimer's dementia. When performed in accordance with the prescribed manipulative steps, the present diagnostic method provides many major benefits and multiple advantages which were not known or available previously. These include the following:

1. The present diagnostic method is a relatively non-invasive procedure which is practiced on the living human individual suspected of or at risk for being afflicted with Alzheimer's disease. The methodology requires and relies upon the use of an automated apparatus and system which can in response to light stimulation accurately monitor pupil constriction velocity over time; and record cumulatively such monitored and measured information as data obtained and sampled over a fixed time interval. The data from the automated system and apparatus can then be mathematically analyzed to provide pupil constriction velocity values over time—a quantitative clinical result which is then preferably compared against a previously established numerical standard range of normal and abnormal values for pupillary constriction velocity. In this manner, a definite, unambiguous, and reliable determination can be made in each instance as to whether or not that living human subject is afflicted with Alzheimer's Disease.

2. The use of automated apparatus to monitor and repetitively measure pupil constriction velocity initiated by light stimulation after pharmacological intervention and the cumulative recording of changes in the constriction velocity provides a large quantum of obtained data which is used as the empirical basis for making a clinical diagnosis and determination. The automated apparatus and systems are able to observe and measure pupil constriction velocity very quickly, extremely accurately, and repetitively.

3. The diagnostic methodology as a whole makes minimal demands upon the patient; does not involve physical exercise or fatiguing manipulations; and avoids the use of systemic medication. Instead, the present methodology relies upon the use of dilute concentrations of neural transmitter mediators such as cholinergic antagonists and agonists. The use of these neural transmitter mediators are in a concentration which does not substantially influence pupillary dynamic responses in a cognitively intact individual; and is insufficient to cause a marked or major change in pupil constriction velocity in a person not afflicted with Alzheimer's Disease. Accordingly, there is little or no probability of any undesirable side effects being generated or felt by the living patient during the course of the diagnostic examination process.

4. The diagnostic methodology which is the present invention may be performed relatively easily and can be completed in its entirety within one hour's time. The diagnostic data are then generated as quickly as the central processing unit of the automated apparatus can operate; and the results appear in printed form or in visual form on a monitor and/or may be transferred to a remote reference facility for final analysis as is most desired or required under these use circumstances.

5. The diagnostic methodology employs a pharmacological manipulation of the pupil of the eye. The preferred method is to apply the neurotransmitter mediator (a cholinergic antagonist) to one targeted eye of an individual being tested for the possibility of Alzheimer's disease; and to compare his/her pupillary dynamic response to light stimulation, the constriction velocity of the pupil, to norms established in advance for a population of preferably age-matched, cognitively intact individuals. A significant difference from the established norm in the pupillary constriction velocity response of such an individual serves to diagnose Alzheimer's disease in that individual.

In order to more easily understand and more fully appreciate the present diagnostic method, the detail disclosure will be presented in sections seriatim and include the following: the principles of the diagnostic methodology; the preferred mode for performing the diagnostic method; parameters and general guidelines for practicing the diagnostic method; first and second preferred protocols for practicing the diagnostic method; and the preferred apparatus and organizational systems useful when practicing the diagnostic methodology.

In addition, to avoid ambiguity in terminology as well as to provide a clear and precise understanding of the scope of the present methodology, a set of specific terms and explicit definitions are given below. These words and their meanings will be employed repeatedly and routinely in this disclosure; and the stated definitions are to be accepted as written and as part of the general lexicon and vocabulary in this art.

Cholinergic: A term pertaining to the neural transmitter acetylcholine. The term is particularly used to designate neurons that release acetylcholine at their terminals, or the physiological effects produced by the stimulation of these neurons, or the acetylcholine receptors on the post synaptic membrane, or chemical agents and drugs that imitate the effects of acetylcholine.

Mydriasis: Dilation of the pupil.

Mydriatic agent: A compound or substance which initiates, induces, promotes or causes pupil dilation.

Miosis: Constriction of the pupil.

Neural Transmitter: A compound or substance that serves to transmit a nervous impulse between cells at a synapse or a neuromuscular junction. Such compounds include but are not limited to acetylcholine, epinephrine, norepinephrine, dopamine, serotonin, y-aminobutyric acid, glycine, and glutamate.

Construction Velocity: The average rate of change in pupil diameter expressed in mm/sec over a given interval of time from initial size to maximal constricted size of pupil.

Re-dilation velocity: The rate of recovery expressed as mm/sec to maximal resting pupil diameter after stimulation by light.

Endogenous substance: A compound or composition developing or originating within the person or arising from causes within the person's body.

Exogenous substance: A compound or composition synthesized, found, or originating outside the person's body.

Photostimulation (visible light stimulation): the purposeful introduction of visible light energy to the eye of a living subject.

Light energy (photoenergy): Electromagnetic radiation of any wavelength including infrared, visible and ultraviolet wavelengths.

Agonist: A compound or substance that imitates, mimics, or acts in a manner similar to the activity or function of a specified tissue, composition or agent.

Antagonist: A compound or substance that blocks the activity or function of a specified tissue, composition or agent.

Mediator: A compound, composition, agent or substance that acts as an intermediary agent to bring, effect, communicate, modify or convey an activity or function in a specified manner.

I. The Underlying Principles Of The Diagnostic Method

The scientific phenomenon and factual basis for the present diagnostic method is the recognition and appreciation that persons afflicted with Alzheimer's dementia are uniquely hypersensitive to the pharmacological effects of neural transmitter mediators, particularly those administered topically to the eye. The existence of such hypersensitivity, however, is not only an intrinsic part of the disease process but also can be intentionally manipulated pharmacologically in the person afflicted with Alzheimer's Disease. Thus, the underlying principles for the present invention are first, that this unique hypersensitive state exists and manifests itself in the autonomic nervous system of the Alzheimer's patient; and second, that this hypersensitive state and condition will manifest itself as an abnormal response to pharmacologically active antagonists and agonists in a distinctive manner which can be utilized for diagnostic purposes reliably and reproducibly.

The present invention reveals that the Aizheimer's disease patient is hypersensitive to cholinergic antagonists. Acetylcholine is endogenous to the autonomic nervous system and is present and functional in neurons and nerve cell bodies which innervate the iris muscle of the eye. However, the purposeful introduction and administration of a neural transmitter mediator such as a cholinergic antagonist or agonist in a concentration which is generally insufficient to cause a marked or noticeable change or modification of pupillary dynamic responses in a cognitively intact individual—will nevertheless cause a major change and marked alteration in pupillary response characteristics in the person afflicted with Alzheimer's Disease.

It is thus essential to recognize and appreciate the two fold criterion which constitutes the present invention's application of the underlying scientific principles: its reliance that an intrinsic part of the Alzheimer's disease process is a hypersensitivity to specific neural transmitters affecting the dynamics and responses of the pupil; and the concomitant view that exogenously introduced pharmacologically active mediators can be employed to manipulate this condition in Alzheimer's disease and to yield an observable hypersensitive pupillary dynamic response—which can be monitored and quantitatively measured. The present invention accepts that these circumstances exist within and throughout the Alzheimer's population generally and thus may properly serve as the basis for making a diagnosis to identify the presence of Alzheimer's Disease in an individual living human.

II. The Hypersensitive Pupillary Dynamic Responses

If and when a person suspected of having Alzheimer's disease is clinically examined, the pupils of the subject typically appear to be similar to those who are cognitively normal. The pupils of the Alzheimer's patient may be examined for size, shape, near response, and consensual light reaction without demonstrating any major defect. Light directed into one pupil will typically result in normal constriction of the pupils in both eyes. As with any population of individuals, some person's pupils may be markedly constricted; others may have unequal pupils; and the visual acuity of the person may be normal, show distant vision, or be near sighted. No casually observed feature of the pupil alone therefore can provide a basis for making a differential diagnosis.

In contrast, the hypersensitive dynamic responses of the pupil in the Alzheimer's disease patient can and do present an observable, reproducible and reliable basis for clinical diagnosis. The state of hypersensitivity of the pupil in the Alzheimer's afflicted subject responds dynamically to the neural transmitter compound (acetylcholine) endogenously present, but also will respond abnormally to unusually small or dilute concentrations of exogenous neural transmitter mediators (cholinergic antagonists and agonists) intentionally introduced to the eye. Equally important, while the pupil of the Alzheimer's patient dynamically responds to these dilute concentrations of neural transmitter modulators, the pupils of cognitively normal persons show little if any change in pupillary response at all.

A range and variety of hypersensitive pupillary responses are individually identifiable and measurable in the Alzheimer's disease patient. For example, as described and claimed in copending U.S. patent application Ser. No. 08/279,797 filed Jul. 25, 1994, the pupillary hypersensitive reaction can manifest itself as an abnormal mydriatic response, pupil dilation, to an unusually small concentration of an anticholinergic agent (such as 0.01% tropicamide); and also be separately expressed as a miotic response, pupil contraction, to an unusually dilute concentration of a cholinergic agonist (such as 0.01% pilocarpine). In these examples, the nature of the hypersensitive pupillary response can be repeatedly observed and quantitatively measured (without any photostimulation) by determining the pupil dilation or by the pupil contraction. The commonly shared event in each of these exemplified instances, however, is the consistent manifestation of the hypersensitive response in the pupil of the Alzheimer's subject. Each format of this manifestation thus provides a reliable basis for clinically diagnosing Alzheimer's disease in a living human subject.

The present invention employs an entirely different manifestation of the hypersensitive pupillary response of the Alzheimer's disease patient to neural transmitter mediators as the basis for making a clinical diagnosis. The hypersensitive manifestation observed, quantitatively measured, and utilized as the test parameter is the change in constriction velocity for the pupil in response to stimulation by visible light as a consequence of introducing a dilute cholinergic antagonist to the eye. The concentration of exogenous neural transmitter mediator (the cholinergic antagonist) administered to the eye of the subject is insufficient to cause any marked pharmacological or physiological change in a cognitively intact normal person; but is adequate to induce and elicit a substantive change in the pupil constriction velocity of the hypersensitive Alzheimer's disease patient. The manifestation thus identifying and distinguishing the Alzheimer's subject is the major change in the constriction velocity of pupil response to photostimulation in comparison to cognitively normal persons receiving the same concentration of neural transmitter mediator. This major hypersensitive difference in the manifestation of the pupillary response to photostimulation therefore serves as a unique and separate clinical response basis for diagnosing Alzheimer's disease in a living human.

III. The Essential Parts Of The Methodology

There are four essential requirements for practicing the diagnostic method which is the present invention. While each requisite part may be performed and satisfied using a variety of different articles and detailed procedures, the requirement is only that the manipulation be achieved regardless of the specific means employed for that purpose.

(1) The method demands the existence and use of non-invasive means for introducing photostimulating visible light of predetermined wavelength and intensity to the eye sufficient to cause a constriction of the pupil; and for determining the velocity of the pupil constriction initiated by the photostimulation. Although a variety of preferred automated apparatus and systems are described in detail hereinafter for achieving these ends and functions, the methodology as a whole is not dependent upon any specific apparatus, instrumentation, electronics, circuitry, optics, or system as such. Accordingly, any means which individually or integrally provides the requisite eye photostimulation and constriction velocity determination will suffice for purposes of practicing the present invention.

(2) The method demands the purposeful administration of at least one neural transmitter mediator to an eye of the person undergoing diagnostic testing. This mediator is an exogenous substance and is a compound selected from the group consisting of cholinergic antagonists and agonists. Moreover, the quantity and concentration of this exogenous neural transmitter mediator to be administered must be sufficiently dilute such that a cognitively normal person receiving this mediator will not show or reveal a marked or substantive change in his constriction velocity after photostimulation.

(3) The method demands that at least one eye of the person undergoing diagnostic testing be subjected to stimulating visible light energy after administration of the neural transmitter mediator to that eye. The range of visible light wavelengths, visible light intensities, time duration of visible light stimulation, and frequency of repeated visible light stimulation may be varied and are described in detail hereinafter. Accordingly, the substantive requirement is only that the eye of the test subject be stimulated by visible light after the introduction of a neural transmitter mediator.

(4) The method demands that the constriction velocity after photostimulation be determined after the neural transmitter mediator has been administered to the eye. This constriction velocity determination can be made using any article, machine, measurement system, method of calculation, and display mode conventionally known or commercially available.

IV. The Diagnostic Method

The Neural Transmitter Mediator

The present diagnostic methodology utilizes the constriction velocity of the pupil in response to stimulation by light of a known wavelength as the observable result, essential diagnostic feature, and type of pupillary dynamic response to be demonstrated by the Alzheimer's disease patient as the hypersensitive consequence and characteristic eye reaction to the administration of a pharmacologically active neural transmitter mediator. Pupil constriction velocity is a dynamic response observed and measured after photostimulation.

In order to utilize pupil constriction velocity as a parameter (rather than any other type of pupillary dynamic change) and as a demonstration of Alzheimer's dementia hypersensitivity, one must administer a dilute concentration of a cholinergic antagonist. A representative, but non-exhaustive listing is provided by Table 1 below.

TABLE 1

Exogenous Neural Transmitter Mediators

Anticholinergic Agents
(cholinergic antagonists)

| Agent-Generic | Name Brand Example | Conventionally Used Doses | Present Use/Comments |
|---|---|---|---|
| Tropicamide | Mydriacyl | 0.5–1.0% | Usually 1.0% |
| Atropine | Atropisol | 1% | Not routinely used for eye examinations in adults. |
| Homotropine Hydrobromide | l-Homatrine | 2% q 10–15 min | Used for refraction not dilation |
| Cyclopentolate Hydrochloride | Cyclogyl | 0.5–2% | 0.5% for fundoscopic examination |
| Scopolamine | Isopto Hyoscine | 0.2–0.25% | Used for post-op mydriasis not eye examinations |

It will be recognized and generally understood by a person ordinarily skilled in the anatomy of the eye that the pupil is formed by the muscles and pigmented stroma of the anterior uveal tract (the iris). There are two types of muscles: a circumferential sphincter found in the margin of the iris, innervated by the parasympathetic nervous system and radial dilator muscles which run from the iris margin to the root of the iris, innervated by the sympathetic nervous system. Pupil size represents a balance between stimulation from the parasympathetic and sympathetic nervous systems. Constriction of the pupil (miosis) is caused by the stimulation of the parasympathetic fibers, whereas dilation (mydriasis) is caused by sympathetic activation. These systems generally contain neurons that are driven by Cholinergic or Adrenergic neurotransmitters respectively. The neuro-physiology of the pupil and iris make it an ideal physiological marker for measuring the integrity of cranial nerve, midbrain and central nervous system functions.

Measurement Parameters And Procedural General Guidelines

A range of general procedural guidelines and measurement parameters are provided herein for the optimization and convenience of both the user and the individual being tested. These general procedural guidelines are provided for the benefit and advantage of the intended user; and these measurement parameters are merely illustrative possibilities, examples and suggestions to consider and use when preparing detailed protocols intended for use on a clinical basis.

The Repetitive Cycle And The Sampling Occasion

An essential part of the present methodology is the use of a non-invasive automated apparatus to monitor the pupillary dynamic changes and to determine constriction velocity (the rate of pupil size changes) after stimulation by a known quantity of visible light energy. Each observation and individual determination of constriction velocity for the pupil constitutes one measurement "episode" or "epoch"; and a measurement episode can be performed in <1–3 seconds repetitively and cyclically. As is described in greater detail hereinafter, the preferred automated apparatus is able to monitor and measure pupil diameter size change repeatedly—both before and after photostimulation—continuously at a rate of about 60 pupil measurements per second. Clearly, however, some automated apparatus can perform the requisite functions at about 10–20 pupil size measurements per second; alternatively, many conventionally available instruments and systems can perform observations and measurement of pupil size change only at much slower rates (e.g., less than 10 pupil measurements per second)—thereby providing quantitatively fewer pupil size measurements over the <1–3 second interval of time allotted as one measurement episode. Accordingly, using the preferred automated equipment described hereinafter merely as a preferred illustrative example, it will be readily recognized and seen that 60 constriction velocity determinations per second will yield a quantum of data which will increase with a longer duration of monitoring and measurement time.

Frequency Of Sampling Occasions

It is deemed desirable that at least two sampling occasions separated by a prechosen length of time be made when practicing the present diagnostic method. The first sampling occasion constitutes the "zero" time and provides the initial baseline characteristics of untreated pupil constriction velocity for that individual patient. It is expected and intended that this initial baseline sampling occasion be made on both the left eye and the right eye of the patient. One eye, randomly chosen, will be the eye treated with the neurotransmitter mediator; and the other eye will be treated with a non-drug control solution.

The present diagnostic method and protocol demands that at least a second sampling occasion be performed after administration of the neural transmitter mediator to the targeted eye, preferably when the maximum change and difference in pupillary dynamic response occurs. The methodology preferably employs minimally two different sampling occasions during which the constriction velocity of the treated targeted eye and also of the non-treated control eye are monitored and measured.

In preferred protocols, however, it is far more desirable that from 3 to about 6 different sampling occasions be performed after introduction of the neural transmitter mediator over a period of about one hour's time. This greater multiple sampling occasion practice is preferable because a number of different time intervals are planned, each of which constitutes one sampling occasion; and the greater number of sampling occasions within the overall protocol will allow a plotting and empirical determination which will more readily and assuredly identify the hypersensitivity of the pupillary response and the greatest change and maximal effects of treating the targeted eye with the chosen neural transmitter mediator. Thus, the preferred protocol will have 6 different sampling occasions of at least 5 measurement episodes each.

Use Concentration of the Chosen Neural Transmitter Mediator

It is most desirable that the user understand and appreciate that he also has a choice of use concentration or strength of agent which will achieve the intended hypersensitive pupillary changes necessary to practice the present diagnostic method effectively and advantageously. This requires some understanding of the underlying axioms governing the choice of use concentration strength for these neural transmitter mediators.

In the preferred mode of practicing the present diagnostic methodology, it is the guiding rule that the use concentration of neural transmitter mediator be such that it will not markedly affect the pupillary dynamic responses of the eye if the person is cognitively intact and is not afflicted with Alzheimer's dementia. The preferred embodiments thus will employ concentrations of a neural transmitter mediator substance which will not cause significant or substantive changes in pupil constriction velocity vs. baseline prior to pharmacological treatment (meaningful changes in the rate of change for pupil diameter size) after photostimulation regardless of the test conditions or use circumstances. This is best shown by use of an illustrative example.

As a representative and prototype example, the preferred mode employs a cholinergic antagonist—tropicamide—in an amount insufficient to cause marked changes in pupil constriction velocity in a person not afflicted with Alzheimer's disease. Empirically, the use concentrations of tropicamide which are insufficient to cause such pupillary dynamic response changes include a range of concentration from 0.0025% to about 0.01%. Thus, a range of use concentrations may be used which include at least the following: 0.0025%, 0.005%, and 0.01%.

Also it will be recalled that in the best mode embodiments, the Alzheimer's disease patient will show a marked hypersensitivity to this use concentration of mediator. However, depending on the concentration of neural transmitter mediator actually used, it is expected and predicted that the amount of time needed before the pupillary dynamic response shows statistically significant differences in the Alzheimer's patient may differ; and thus the time of maximal response may vary somewhat. For example, it is theoretically estimated that a use concentration of 0.005% tropicamide will consequently result in a maximum change in constriction velocity at about 25–29 minutes after its administration to the targeted eye in an Alzheimer's patient.

Constriction Velocity Determination Cycles

The calculation of pupil constriction velocity is made using pupil diameter size data obtained both before and after photostimulation. Each cycle of repetitious measurement includes a first pupil diameter size determination, followed by photostimulation, and then a measurement of the stimulated (constricting) pupil. The pupil is then allowed sufficient time to re-dilate to its original diameter size state; and another measurement cycle to determine constriction velocity is then initiated. The preferred automated instruments described hereinafter can perform 5–60 pupil size measurements per second.

The initial and follow-up measurements of pupil size in each measurement episode are preferably made using near infra-red light; and employ both the apparatus and procedures described within U.S. Pat. Nos. 4,755,043 and 5,187,506, the texts of which are expressed incorporated by reference herein. Sources providing wavelengths of about 800 nm–2000 nm are used; and wavelengths from about 850 nm to 900 nm are deemed best. The light intensity is adjustable and preferably lies in the range of 1.5–6.5 mw/cm$^2$.

Basis For Comparing The Empirically Obtained Data in Order To Diagnose Alzheimer's Disease A diagnosis is preferably made when the pupil constriction velocity of the eye treated with either a cholinergic antagonist or agonist changes substantially and is significantly different than a predetermined range of numerical values representative of the cognitively intact population as a whole. The difference from the normal standard range of numerical values is considered the diagnostic criterion for determining the presence or absence of Alzheimer's disease in a living human individual. This diagnostic evaluation is empirically determined by examining the percentage change in pupil constriction velocity of the eye results of known (presumptive) Alzheimer's patients and of known cognitively intact individuals to a particular neural transmitter substance at a particular strength concentration; and determining the point at which known Alzheimer's patients compared to known cognitively intact individuals are separable and distinguishable in the magnitude of their response to the test as measured by the percentage change in pupil constriction velocity.

V. Preferred Protocol

The diagnostic method which is the present invention employs non-invasive automated apparatus and systems which can observe and repetitively determine pupil constriction velocity over short time intervals in an uninterrupted manner. The manner of observation and repetitious measurement seriatim yields constriction velocity determinations of from about 5–60 measurements per sampling occasion. Since the different automated systems may vary in their speed of measuring pupil size changes, and the time duration of each sampling occasion may be extended or shortened, representative protocols using different instruments are presented below.

It will be recognized and appreciated also that the preferred protocol presented herein is merely illustrative of the diagnostic methodology as a whole. The preferred protocol is intended and envisioned to practice the different modes of use described previously herein as well as to accommodate the different automated equipment and clinical use circumstances in which persons suspected of being afflicted with Alzheimer's disease are to be encountered.

A Preferred Protocol For Performing The Diagnostic Methodology (A). Prior to administering the pupil assay, the following patient screening tests must be done.

1. Evaluate the patient for any ocular abnormalities:
   a. cataracts.
   b. history of glaucoma.
   c. a narrow anterior chamber.
   d. local corneal pathology that might affect corneal permeability (e.g., dry eye or poor tear lakes.
2. If patient exhibits condition "b, c, or d" do not proceed with the test.
3. If patient has cataracts that distort the shape of the pupil excessively do not administer the neural transmitter mediator to the affected eye.
4. Screen patients for any current use of drugs with central or peripheral cholinergic effects. If patient is currently using medications with known cholinergic effects, note on the patient record for future reference in interpreting pupil assay data.

(B). Once screening has been done insure that the patient is alert and not agitated or drowsy. If patient is excessively drowsy do not proceed with test, but schedule the patient for future testing.

(C). Allow five minutes for patient to sit quietly while pupils adjust to ambient photopic illumination at no greater than 5 foot candles in the examining room.

(D). After five minutes image the patient's eye with a 1050 Pupillometer eye measurement system. Set the pupil discriminator such that the eye is completely encircled with the white discriminator and forms a clean elliptical image in the center of the pupil monitor. Open a data file and begin recording pupil diameter data. Stimulate the eye by means of the photostimulator and continue to record data. Repeat this process after five seconds rest each time for an additional five measurement episodes. Repeat the entire procedure for the untreated eye.

(E). After completing the baseline readings and saving this data to a file, administer a single drop of the chosen neural transmitter mediator in the appropriate use concentration (e.g., a 0.01% tropicamide solution) to one targeted eye chosen arbitrarily. The drop should be administered in the following manner.

1. Have the patient in a position on a chair or an examining table so that they can tilt their head well back.
2. Hold open the lower and upper eyelid with the thumb and first finger.
3. Squeeze the bottle of treatment solution gently so as to allow a single drop to fall on the center of the lens of the eye.
4. Have the patient close his/her eye after administration of the drop.
5. Administer gentle pressure on the inner canthus of the eye for 1 minute to prevent excessive entry into the systemic circulation.

(F). After 1 minute have the patient sit up. Wait one minute for the eye to adjust to ambient illumination and proceed to image the pupil as described in (D) above. Record 5 seconds of pupil constriction velocity determinations separated by 30 second intervals to a data file.

(G). Repeat the procedure in steps (E) and (F) with the other non-treated eye but using a single drop of sterile water for ophthalmic use.

(H). After administration of the sterile water drop to the non-treated eye and measurement of the non-treated pupil have the patient wait quietly for a period of 5 minutes.

(I). After 5 minutes have elapsed, wait for 1 minute while the patient's eye accommodates to the low illumination. Proceed to image the eye again as described in step (F). Record five constriction velocity measures from the treated eye. Repeat this procedure with the un-treated eye.

(J). Repeat the pupil constriction velocity determination procedure every 5 minutes until minute 30 of the test.

(K). After the last reading at test minute 30, have the patient wait for 10 minutes more. After 10 minutes, again record pupil constriction velocity determinations from the treated and un-treated eyes as described above.

(L). Have the patient wait a final 10 minute segment and then record pupil constriction velocity determinations from the treated and un-treated eyes as described above. The final reading should be taken approximately 55 minutes after administration of the eye drops.

VI. Automated Instruments and Systems Suitable For Measuring Pupil Constriction Velocity A variety of non-invasive automated apparatus is known and commercially available which can be used as is or modified quickly to meet the minimal operating requirements necessary for practicing the present diagnostic method. Exampling such conventional apparatus are U.S. Pat. Nos. 4,755,043; 5,187,506; and 4,850,691. In addition, there is a varied class of instruments for measuring pupil diameter which are generally termed "pupillometers." A typical pupiilometer measures, displays, and records pupil diameter before and after a light stimulus causes a constriction of the pupil. These instruments can use light stimuli to constrict and/or dilate the pupil artificially; and also be modified to extend the typical manner of usage from making a single measurement to making repetitious measurements seriatim over a prechosen time duration in an uninterrupted manner. However, insofar as is known to date, none of these conventional systems have been employed for the diagnosis of Alzheimer's disease; and none of the requisite software have ever been modified or employed clinically for such a diagnostic purpose.

The primary goal and essential function for using automated instruments and systems is the multiple measurement of pupil constriction velocity in a serial and repetitive manner which will yield a major increase in the quantum of empirical denominations (at each measurement occasion). The apparatus described herein can determine pupil constriction velocity every 1–3 seconds; and repeat this technique cyclically for a short or an extended time period over a desired number of seconds or minutes in duration. Thus, these instruments and systems provide pupil constriction velocity determinations for as long as deemed necessary or desirable under the clinical testing parameters. It is for these reasons that these non-invasive instruments and systems are essential for use when practicing the present invention.

A First Non-Invasive Apparatus

A Photostimulator/Controller In Combination With A TV Pupillometer

Component 1

The Series 1000 Photostimulator and Controller is a powerful device for test involving the placement of controlled and programmed pulses of stimulus light into one or both eyes of a subject. The beams of light are controllable in exposure frequency, pulse width, focus, beam diameter and intensity. The Photostimulator/Controller is suitable for pupillometry tests where the responses of pupil diameter to a light stimulus under various subject conditions are measured and evaluated.

For pupillometry, the Photostimulator/Controller may be used with the companion Applied Science Laboratories Series 1050 TV Pupillometer. An illustration of the combined apparatus is shown by FIG. 1. One or both eyes may be light stimulated; and the controls for the two eye channels may be synchronized in any desired phase and temporal relationship in order to test binocular responses.

Within the Series 1000 Photostimulator/Controller device, there is an integrated aiming capability for placement of the light beam on the subject's pupil. Focusing produces a parallel beam or allows beam focus on some other plane in or out of the eye, e.g., a Maxwellian view. A general purpose filter holder is provided for the insertion of any desired filter and may be conveniently moved out of the way when not in use. A neutral density wedge may also be used for continuous intensity control. A virtual point source tungsten concentrated arc lamp is used with appropriate optics to provide the collimated beam of light.

The controller provides a very convenient way of programming the shutter exposure times for one or two channels. The pulse width and the period may be controlled for each channel, and the phase relationship between the two systems can also be determined. This provides virtually any pulse profile that may be desired. Continuous cyclic operation or single pulse actuation is possible. The two channels may be locked phase or randomly related.

The photostimulator is suitable for measurements of pupil diameter response to light stimuli under various testing conditions.

| | Series 1000 Photostimulator Specifications: |
|---|---|
| Lamp | Sylvania lamp type C2T; 2 watt tungsten concentrated arc lamp; .007 m mean light source diameter; 0.30 average axial candle power; 150 hours average life. |
| Spectrum (wave length) | 0.7–2.1 microns |
| Lens | 50 mm fl. 4 c mount |
| Light Beam Diameter | 1 mm to over 14 mm with parallel beam. |
| Focusing Capability | The light beam may be focused at any distance from the Photostimulator, from 1 inch away from exit mirror to infinity. |
| Shutter | Two leaf integral shutter with 14 mm aperture. Other shuttering modes are available. |
| Filter Holder | Accepts standard 2" × 2" filters. It may be swung out of the optical path. |
| Aiming Mechanism | 2-axis aiming by use of two orthogonal fine controls. |
| | Series 1000 Controller Specifications: |
| Channel 1 | Pulse Width: Thumbwheel switch digital control from 0.1 to 9.9 seconds. Pulse Duration: Thumbwheel switch digital control from 0.1 to 99.9 seconds. |
| Channel 2 | Pulse functions same as Channel 1. |
| Interchannel Phase | Channel 2 timing may be independent of Channel 1 or coupled so that Channel 2 timing operates with a delay from Channel 1. Delay may be set from 0.1 to 99.9 seconds. |
| Cycling Mode | Single cycle or continuous. |

Component 2

The Model 1050 TV pupillometer provides accurate real-time measurement and display of pupil diameter. The pupil is continuously monitored: pupil diameter is shown directly on a panel meter; and pupil diameter is shown in digital and analog forms. Pupil diameter measurement is independent of eye movement and other variations over a large field of view.

Principles Of Operation

The TV pupillometer uses a near infrared illuminator and a low light level, solid state CCD television camera to observe the eye. A pupil recognition circuit automatically acquires the pupil from the iris, the eyelids, and other noise with minimum operator adjustment. A television monitor displays the image of the eye with superimposed pupil delimiters to clearly indicate the accuracy of the measurement. The automatic circuitry will maintain proper measurement for a large range of settings and conditions.

Pupil diameter is presented as a direct readout on the analog panel meter with a scale of 0 to 10 mm. Optional chart recorders are available to record pupil diameter with either the full 0 to 10 mm range or an expanded sub-interval of the measurement range. An external pupil diameter output signal, scaled at 1 V/mm diameter, and a digital output signal are furnished on all models.

In operation, the subject's head is usually stabilized by a chin rest or a chair with a headrest. There must be an unobstructed visual path to the eye. The operator then adjusts the optics and monitor to obtain a clear image of the subject's eye. Afterwards, the operator adjusts the discriminator control until a crescent appears at the left edge of the pupil and delimiters appear in the monitor above and below the pupil. As long as the delimiters are properly positioned, the measurement of pupil diameter is correct, in spite of any other noise or artifacts. Pupil diameter in millimeters is displayed on a panel meter and provided as analog and digital signals. Pupil diameter size is usually measured vertically; however, horizontal diameter and pupil area measurement are also possible.

The TV pupillometer system is available as a monocular system to monitor one eye or as a binocular system composed of two mechanically, electronically, and optically integrated pupillometers capable of functioning together or independently. The binocular system can be used to monitor the pupil diameters of both eyes simultaneously.

TV Pupillometer Specifications

Allowable eye movement: Horizontal 30; 40 or higher with reduced accuracy. Eyelids may limit this range with some subjects.

Pupil diameter measurement range: 2.0 to 10 mm or higher (normal physiological range for humans is 2.9 to 6.5 mm). Non standard ranges can be accommodated; consult factory.

Measurement resolution: 1 TV scan line; 500(600) full scale.

Accuracy: Better than 0.5 mm or ½%.

Noise: 0.01 volt or 0.01 mm with model pupil.

Linearity: Analog and digital outputs, better than 0.01 mm or 1%; meter, better than 0.2 mm or 2%.

Sampling rate: 60(50) per second. Output is averaged every two fields, i.e., each ⅟30th(⅟25th) of a second. Non averaged output is also available.

Illumination: Near infrared, filtered, incandescent lamp illumination, centered at 8500 Angstroms.

Operator setting indicators: Discriminator crescent appears on monitor at edge of pupil, along with delimiters above and below as determined by a pupil recognition circuit. The proper position of the delimiters indicates to the operator that the measurement is being performed correctly.

Power requirements: 105–125 V AC, 50–60 Hz; optional 230–250 V AC, 50 Hz.

A Second Non-Invasive Apparatus: The PUPILSCAN System

Whereas Model 1050 offers accuracy, maximum system flexibility, and high sampling speed, the S-6 and S-7 devices offer simplicity of use, portability, and automatic data recording and display. The S-6 and S-7 devices are ideal for clinical or field studies primarily concerned with pupillary reflex function and fast subject throughput.

The S-6 device, also know as the PUPILSCAN™ apparatus, is a binocular tabletop device that can be self operated by the test subject. Both devices are interfaced to any IBM compatible PC via a conventionally supplied interface board and cable.

Figure 2:
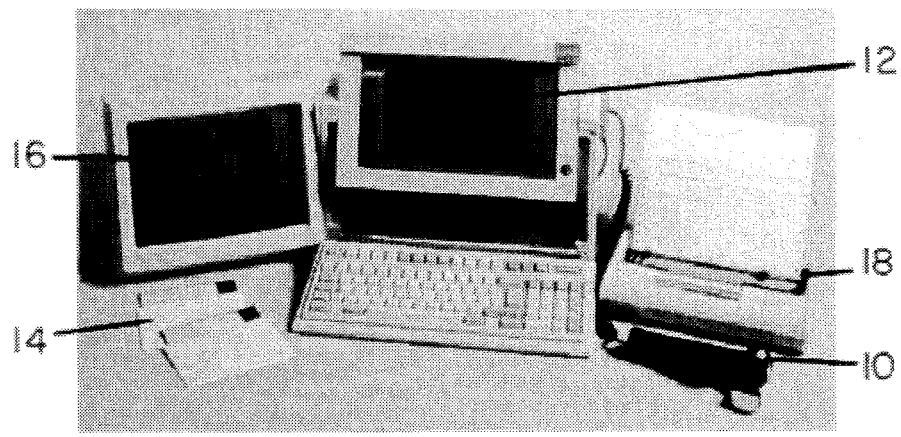
FIG. 2 is a photograph showing the S-6 complete assembly and system.

The S-6 system device, the PUPILSCAN apparatus, is a compact, lightweight automatic instrument that plugs into a circuit board in any IBM compatible personal computer. The S-6 system offers accurate, quantitative and dynamic measurement of pupil diameter size and reflex by infrared scanning, with data capture, analysis, recording, display, and printout in flexible formats. The complete system is shown by FIG. 2 and includes a PUPILSCAN Optical Unit 10, IBM PC or compatible computer 12, program floppy disks 14, an optional auxiliary monitor 16 and a printer 18.

Figure 3:
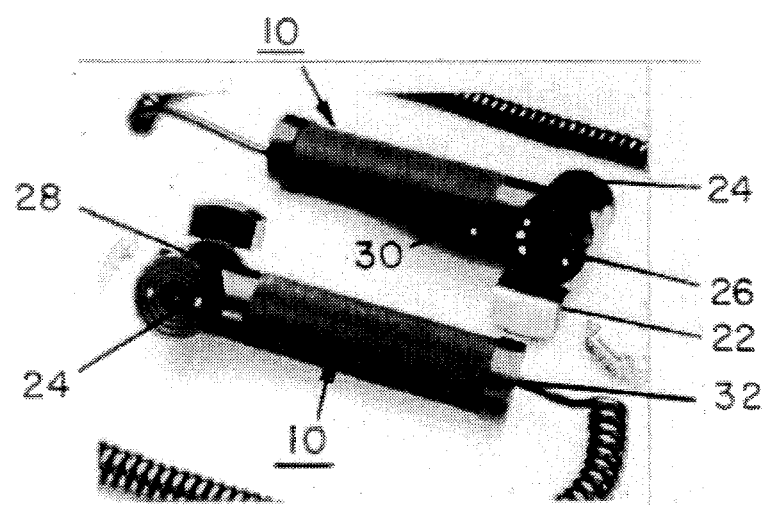
FIG. 3 is a photograph showing the unassembled component parts of the S-6 optical unit.

The unassembled component parts of the S-6 Optical Unit 10 itself are shown by FIG. 3. These include an eye illuminator 22, an image sensor illuminator 24, a light stimulus pulse unit 26, an alignment aid 28, a scan rate activating switch 30, and a hand-size containment handle 32.

Principle Of Operation

When the trigger position operating switch on the S-6 optical unit is depressed, infra-red illumination is turned on and a reflected image of the pupil is focused on an electronic image sensor. The illumination is adjusted automatically by the program to the optimum level for any eye, simplifying use under widely variable ambient light conditions. To aid in centering the instrument on the pupil, a pair of red diodes on the cross hair ring are illuminated or extinguished when satisfactory image position has been achieved as a signal to the operator to release the operating switch to make the measurement. When the switch is released, the program fine tunes infra-red illumination and automatically fires selectable intensity green diodes for a programmed duration stimulus pulse.

Figure 4:
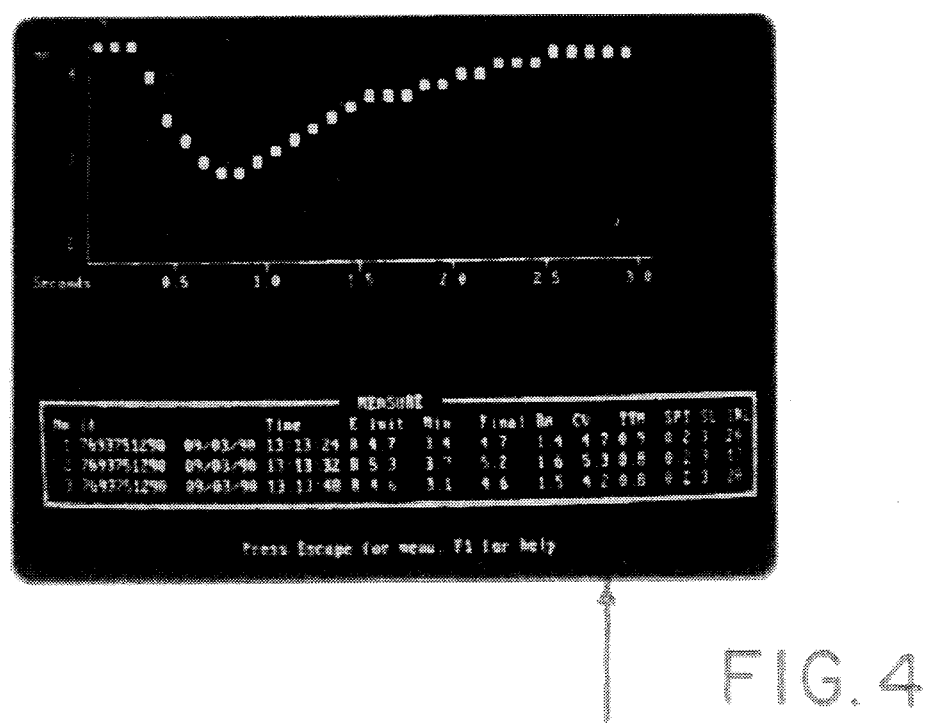
FIG. 4 is a photograph showing the screen display of measurement data using the complete S-6 assembly and system.

The solid state image sensor is scanned at either 10 or 20 times a second (as chosen when configuring the operating program) and "at rest" pupil diameter, minimum diameter produced by the stimulus pulse, "recovered" diameter at the end of a selectable number of scans and elapsed time from start of the stimulus pulse to the minimum diameter appear on the monitor screen as digital data in millimeter and seconds units, respectively. Maximum velocity of constriction is also displayed in millimeter per second and the amplitude of pupil constriction is calculated and displayed. The screen display of measurement data is shown by FIG. 4.

In addition, a time plot or pupil response curve appears automatically at the end of each measurement cycle. The plot for subsequent determinations replaces the previous curve and digital data are added beneath those of earlier cycles for easy comparison of successive data measurements. The plot display is also shown by FIG. 4.

All data are time and data stamped by and may be recalled to the screen for review, printed or saved in a user-named file for later analysis by importing into a spreadsheet/graphics program. Pupil constriction velocity vs time plots may be printed directly without leaving the measurement mode or at the conclusion of a set of measurements. Saved measurement data may be recalled and additional measurements may be added to the file allowing comparison of current data with measurements from an earlier session, creation of a cumulative patient history, etc.

| SPECIFICATIONS--Type 6 Optical Unit | | | |
|---|---|---|---|
| Dimensions | L<br>190 mm<br>7 ½" | W<br>50 mm<br>2" | H<br>32 mm<br>1 ¼" |
| Weight | 285 gm../10 oz. | | |
| Image Sensor | 65K rectangular pixel array. | | |
| Eye Illumination | Yellow diode (1) 583 nm peak wavelength. Typical intensity 1 foot-candle. | | |
| Image Sensor Illumination | Infra-red emitting diodes (4) 880 nm peak wavelength. Intensity adjusted automatically by software in range 1.5 mw/cm² to 6.5 mw/cm². | | |
| Stimulus Pulse | High intensity green diodes (2) 565 nm peak wavelength. Intensity selectable in 3 steps in range 3 to 13 foot-candles. Pulse duration programmable in 0–1 second steps from 0 (no pulse) to 10 seconds. Reprogrammable in MEASURE mode. | | |
| Alignment Aid | Red diodes (2) on handle centerline indicate direction to move to center instrument on pupil. | | |
| Pupil Image Display | On computer monitor, software selectable, and on auxiliary monitor with Type 6EV circuit board. | | |
| Scan Rate | 10/second or 20/second, software selectable. | | |
| Actuating Switch | Push button; depress to turn on illumination, release to start automatic measurement/stimulus cycle. Can also start measurement cycle from computer keyboard. | | |
| Material | Hand-size handle, viewing tube, cross hair ring and rotating cheekrest in black Delrin ™. | | |
| Driver Circuit Board | PUPILSCAN Type 6 circuit board (⅔ industry standard length) or Type 6EV (full length industry standard card); installs in expansion slot in IBM PC or compatible personal computer (½ length industry standard card). | | |
| Software | Operating programs are menu-driven PC-DOS or MS-DOS executable files with help screen supplied on either 5 ¼" or 3 ½" floppy disks.<br>Configurable from menu to allow selections to match computer hardware and to set default measurement parameters.<br>Measurement data and response plot of each record can be reviewed; data and plots are printed from menu and stored to disk.<br>Data analysis via popular spreadsheet/graphics/database programs or unique PUPILEX program. | | |

A Third Non-Invasive Apparatus: The PUPILSCREEN System

The S-7 device or PUPILSCREEN™ instrument is designed for convenient binocular measurements. A knob on the device quickly alternates the measurement from left to right eye. Consensual stimuli conditions are set up at the touch of the computer keyboard.

The PUPILSCREEN™ system and instrument requires a power and control interface board that plugs into any IBM compatible PC but slot. The standard Type 6 board is a ⅔ long PC board. The optional Type 6-EV board is full length and allows an image of the pupil to be obtained at an external and remote TV monitor.

Output Formats

The PUPILSCREEN™ devices are designed to automatically display pupil images and pupillary reflex graphs on a computer screen. Computer files are created which can be further manipulated by user programs or the optional spreadsheet analysis templates which we offer. The data in the files may also be output through the PC's RS232 serial port (COM1).

Figure 5:
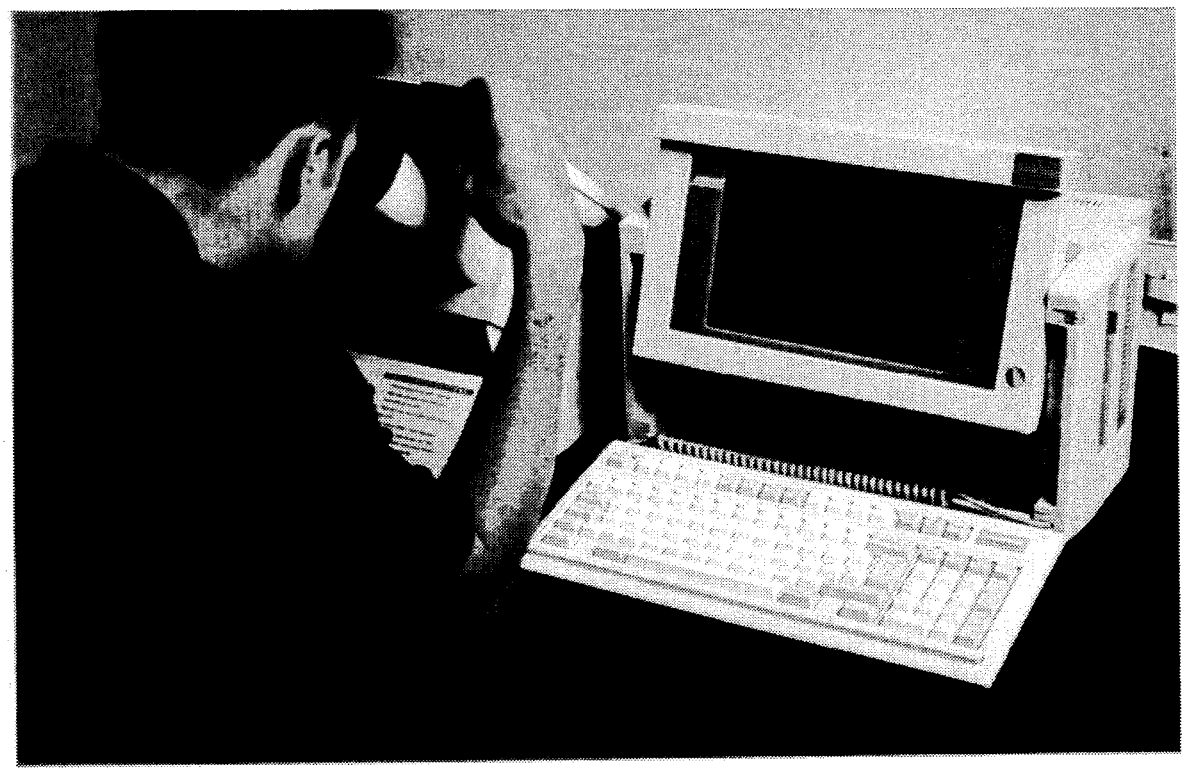
FIG. 5 is a photograph showing the complete S-7 instrument assembly.

The S-7 instrument assembly functions on a plug-in accessory to an IBM PC or compatible personal computer; is operated by an easy-to-use, menu-driven, program, offering a range of programmable measurement variables; and provides for automatic storage of pupil measurement data as well as retrieval and analysis of subject data from a database for rapid comparisons with previous or baseline measurements. The S-7 device is a table-top instrument ideal for large volume screening tests in which the subject aligns his eyes with aid of a video image of the pupil. Once aligned, the subject himself presses a switch to initiate an automatic single or multiple cycle measurement sequence. An illustration of the complete system appears in FIG. 5.

Figure 6:
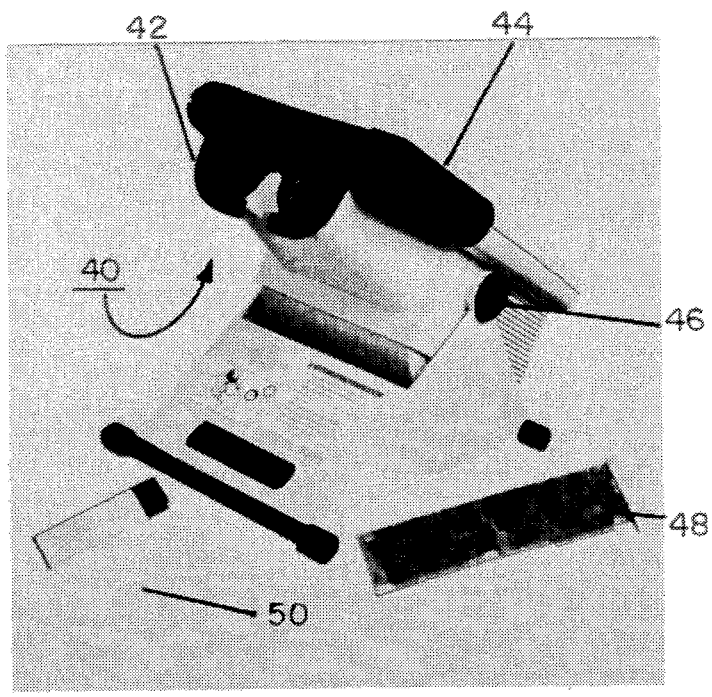
FIG. 6 is a photograph showing the S-7 optical instrument.

The PUPILSCREEN optical instrument 40 is shown by FIG. 6. The device 40 itself is a binocular eyepiece unit 42 having a facial rest support which surrounds the eyepiece; hand grips and an operating switch 44; a pivot with locking knobs 46; a driver circuit board 48; and a program disk 50.

Operating Principles

The PUPILSCREEN optical unit is controlled by a circuit board installed in an expansion slot in an IBM or compatible personal computer. The circuit board also allows a real time image of the pupil being measured to be displayed on the computer monitor. This allows an operator to coach first time users through the measurement sequence with reference to the pupil image he can see on the computer monitor. Circuit board Type 6EV circuitry includes components to display a real time image of the pupil on an external monitor in addition to the host computer display. The operating program has facility to operate the instrument entirely from the computer keyboard so the subject role may consist simply of positioning himself at the optical unit and the operator may control the entire measurement sequence. The external monitor image can be used as a training aid to give subjects a preview of the pupil image and the technique used to center the image for consistently good measurements.

Once the eye to be measured is set by rotating the selector knob on the top of the unit, subject identification is entered from the computer keyboard in response to a screen prompt. The subject positions his head against the foam rubber face pad and fixes his gaze straight ahead where the pupil image will be displayed in the optical unit. The subject then initiates the measure cycle by pressing a switch.

Figure 7:
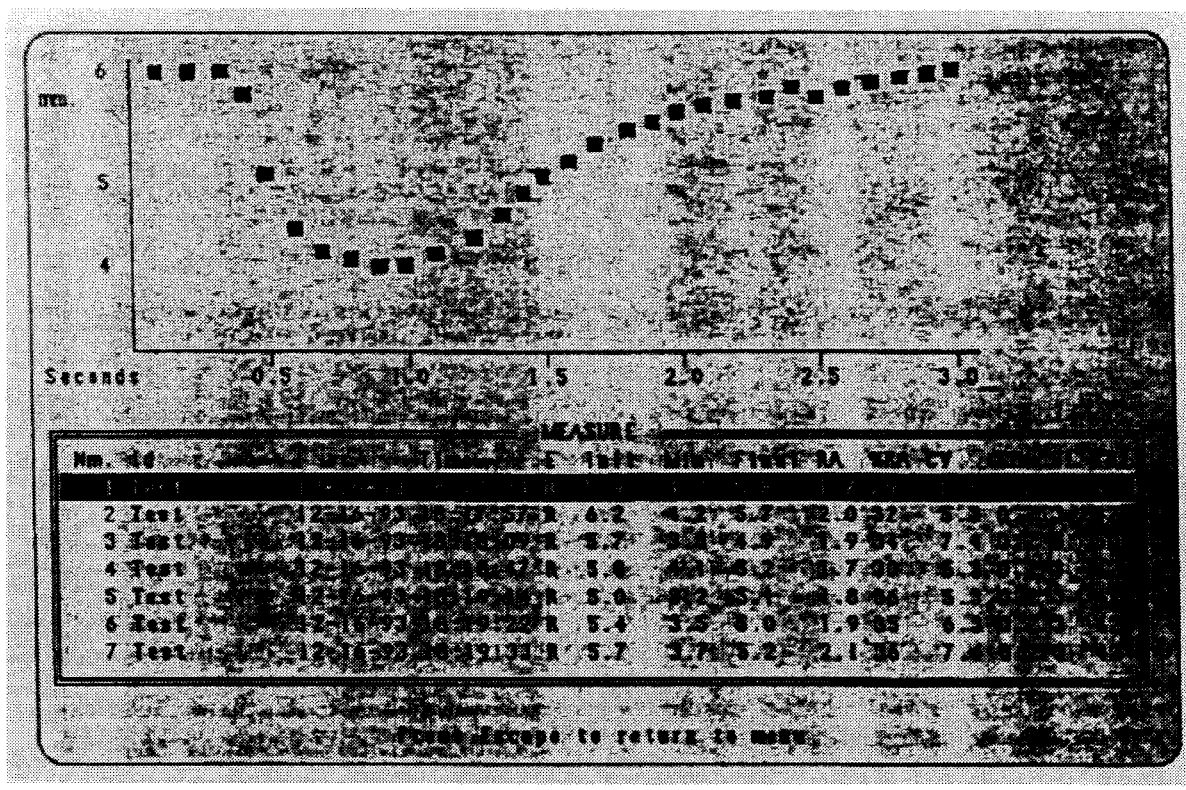
FIG. 7 is a photograph showing the monitor display of the S-7 assembly and system.

After each measurement cycle the computer monitor will display the pupil response curve and the key parameters of pupil size and response characteristics will appear on the monitor display. An example of a computer monitor display showing the measured results is given by FIG. 7.

Each additional measurement cycle will be recorded and displayed independently on the monitor. Notice that each new record is assigned a serial number and is placed below previous measurement(s). The eighth measurement will cause the data for the first to be scrolled off, displaying a maximum of seven consecutive records. There is no limit to the number of measurements for any subject.

After experience is gained with the single measurement cycle, the program may be reconfigured for multiple measurements. Experimentation may be required to fix the optimum interval between measurements. The objective, of course, is to shorten the overall cycle as much as possible to avoid subject boredom and fatigue but to allow a reasonable pause for the subject to blink and rest the eye.

| PUPILSCREEN Instrument Specifications: | | | |
| --- | --- | --- | --- |
| Dimensions | L | W | H |
| | 435 mm | 267 mm | 262 mm |
| | 17 ⅛" | 10 ½" | 10 ⅜" |
| | Pivots through 80 degrees to suit subject height. Friction locking knobs on both sides. | | |
| Weight | 7 Kgs./15.4 lbs. | | |
| Image Sensor | 65K rectangular pixel array. | | |
| Image Sensor Illumination | Infra-red emitting diodes (4) 880 nm peak wavelength. Intensity adjusted automatically by software in range 1.5 mw/cm$^2$ to 6.5 mw/cm$^2$. | | |
| Stimulus Pulse | High intensity green diodes (2) 565 nm peak wavelength. Intensity selectable in 3 steps in range 3 to 13 foot-candles. Pulse duration programmable in 0–1 second steps from 0 (no pulse) to 10 seconds. Reprogrammable in MEASURE mode. | | |
| Alignment Aid | Real time pupil image display on amber CRT; external brightness control. | | |
| Pupil Image Display | On computer monitor, software selectable. | | |
| Scan Rate | 10/second or 20/second, software selectable. | | |
| Actuating Switch | Push button; depress to turn on illumination, release to start automatic measurement/stimulus cycle. Software permits programmable number of automatic measurement cycles with programmable length interval between measurements with one switch depress/release action. | | |

| | -continued |
|---|---|
| PUPILSCREEN Instrument Specifications: | |
| Material | Beige plastic housing with black foam rubber grip pads and facial rest. Integral carrying handle. Non-skid rubber feet. Optional black nylon carrying case. |
| Driver Circuit Board | PUPILSCREEN Type 6 circuit board (⅔ industry standard length); installs in expansion slot in IBM PC or compatible personal computer (½ length industry standard card). |
| Software | Operating programs are menu-driven PC-DOS or MS-DOS executable files with help screen supplied on either 5 ¼" or 3 ½" floppy disks. Configurable from menu to allow selections to match computer hardware and to set default measurement parameters. Measurement data and response plot of each record can be reviewed; data and plots are printed from menu and stored to disk. Data analysis via popular spreadsheet/graphics/database programs or unique PUPILEX program. |

The present invention is not to be restricted in form nor limited in scope except by the claims appended hereto.

What we claim is:

1. A non-invasive method for diagnosing Alzheimer's disease in a living human subject, said diagnostic method comprising the steps of:

providing non-invasive apparatus means for
   (a) introducing photostimulating visible light of predetermined wavelength and intensity to the eye on-demand sufficient to cause a constriction of the pupil, and
   (b) determining the velocity of pupil constriction caused by said introduced photostimulating visible light;

identifying one eye in the living human subject as a targeted eye;

administering at least one neural transmitter mediator to said targeted eye of the living human subject in an amount insufficient to cause a marked change in pupillary dynamic response in a person not afflicted with Alzheimer's disease, said neural transmitter mediator being selected from the group consisting of cholinergic antagonists and agonists;

waiting a predetermined interval of time for said administered neural transmitter mediator to act upon said targeted eye; then introducing photostimulating visible light of predetermined wavelength and intensity to the targeted eye sufficient to cause a constriction of the pupil using said non-invasive apparatus means; and determining pupil constriction velocity for said photostimulated targeted eye using said non-invasive apparatus means, a marked decrease in pupil constriction velocity for said targeted eye with respect to a pre-established normative standard diagnostically establishing that living human subject as being afflicted with Alzheimer's disease.

2. The diagnostic method as recited in claim 1 wherein said neural transmitter mediator is an agent selected from the group consisting of tropicamide, atropine, homotropine hydrobromide, cyclopentolate hydrochloride, and scopolamine.

\* \* \* \* \*